United States Patent [19]

Ishijima

[11] 4,165,461
[45] Aug. 21, 1979

[54] DETECTING APPARATUS FOR INSERTS, THICKNESS UNEVENNESS OR IMPURITIES

[75] Inventor: Hiroshi Ishijima, Tokyo, Japan

[73] Assignee: Kabushiki Kaisha Daini Seikosha, Japan

[21] Appl. No.: 809,437

[22] Filed: Jun. 23, 1977

[30] Foreign Application Priority Data

Jun. 23, 1976 [JP] Japan .................... 51-74162

[51] Int. Cl.² .................... G01N 23/00; G02B 5/00
[52] U.S. Cl. .................... 250/359; 250/505; 250/358 T
[58] Field of Search .............. 250/272, 273, 277, 308, 250/358 R, 358 T, 359, 360, 363 S, 505

[56] References Cited

U.S. PATENT DOCUMENTS

| | | | |
|---|---|---|---|
| 3,452,193 | 6/1969 | Petersen | 250/358 |
| 3,840,747 | 10/1974 | Macovski | 250/505 |
| 3,854,046 | 12/1974 | Wood | 250/358 |

Primary Examiner—Alfred E. Smith
Assistant Examiner—Janice A. Howell
Attorney, Agent, or Firm—Robert E. Burns; Emmanuel J. Lobato; Bruce L. Adams

[57] ABSTRACT

Radiant rays irradiated from the source penetrate through an object in which inserts or the like are disposed at some distances. A radiant ray detector is provided at the opposite side of the object to the source to detect the radiant rays passed through and somewhat absorbed in the object. A slit or collimator is arranged movable along the object between the source and the detector. The output of the detector changes in accordance with the travel of the slit since the absorption coefficient of the inserts is different from that of the matrix. The output is displayed with a graphic display and further is operated into digital signals for computer input or indicating. The position signal of the slit is used for the display and for digital indicating.

12 Claims, 3 Drawing Figures

4,165,461

DETECTING APPARATUS FOR INSERTS, THICKNESS UNEVENNESS OR IMPURITIES

BACKGROUND OF THE INVENTION

This invention relates to apparatus for detecting in a body inserts, thickness unevenness or impurities such as air, metal or the like which have different radiant ray absorption coefficiencies from that of matrix material. All such discontinuities are for convenience herein referred to as inserts.

In prior radiography for detecting inserts, impurities or thickness unevenness of molding, welding or sheet, there are provided a radiant ray source placed facing the object to be inspected and an X-ray film arranged along the object opposite to the radiant ray source for detecting X-ray distribution which is projected there by way of the object. This method requires developing process of the film which requires much time, and further requires much film and is expensive for wide area inspection. Therefore, it cannot be availed to the inspection of sheet on line of a plant.

BRIEF SUMMARY OF THE INVENTION

It is an object of the present invention to provide a detecting apparatus for inserts, thickness unevenness or impurities in matrix material, with which real-time inspected data are displayed or recorded.

It is another object of the present invention to provide a detecting apparatus for inserts, thickness unevenness or impurities in matrix material, which does not require much expense.

It is a further object of the invention to provide a detecting apparatus for inserts, thickness unevenness or impurities in matrix material, which is suitable for the inspection of running sheet on a processing line.

It is a still further object of the invention to provide a detecting apparatus for inserts, thickness unevenness or impurities in matrix material of steel cord tire, with which steel cord pitch and/or steel cord density (cord number per unit width of calendared tire belt) can be determined accurately.

DETAILED DESCRIPTION OF THE PREFERRED EMBODIMENT

A preferred embodiment of this invention will be described referring to FIGS. 2 and 3.

Figure 1:
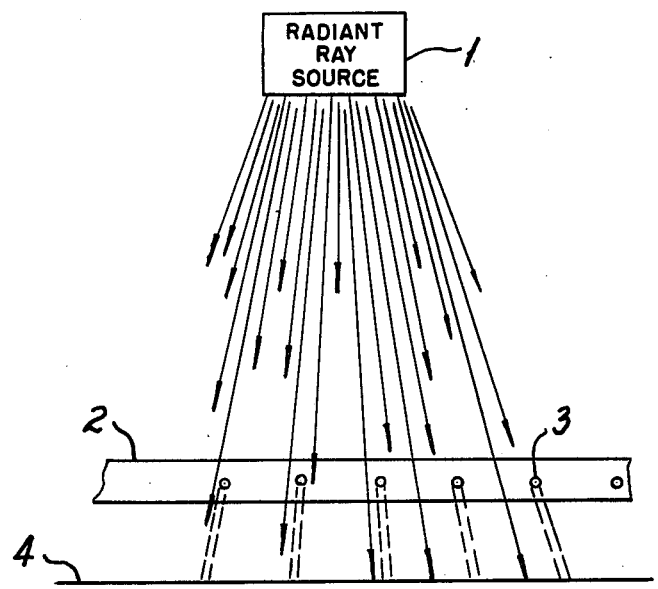
FIG. 1 is a schematic view of a conventional radiographical detecting apparatus.
Figure 2:
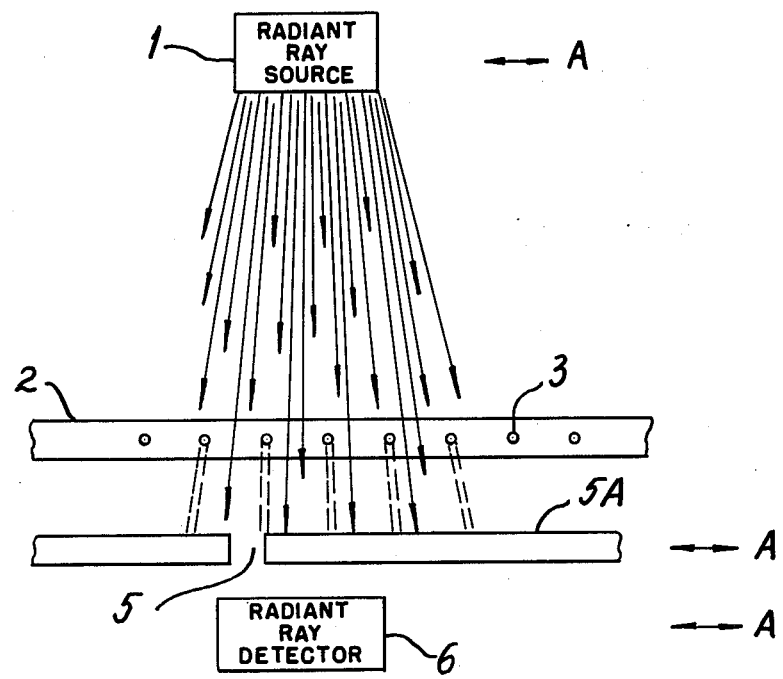
FIG. 2 is a schematic view of a detecting head device in the detecting apparatus according to the invention, by which a sheet is inspected.

FIG. 2 shows a detecting head device inspecting a sheet object, in which numeral 1 designates a radiant ray source (X-ray or γ-ray source). Radiant rays penetrate through a sheet 2 and are attenuated by sheet 2 and inserts 3, inserts 3 having much more absorption coefficiency of the rays than the matrix of sheet 2. A radiant ray detector 6 is disposed opposite to radiant ray source 1, inserting a slit frame 5A with sheet 2, so as to detect the penetrated and attenuated radiant rays by way of a slit 5 of slit frame 5A. The frame 5A is made of radiant ray non-transmissive material such as thick steel board, lead board or heavy metal board. The slit is preferably much narrower than inserts 3 in width. Sheet 2 is a calendered steel tire belt on a processing line, and is running in its longitudinal direction (i.e. perpendicular to the paper sheet). The combination of radiant ray source 1, slit frame 5A and detector 6 is fixed in a body and is to synchronously run from side to side across sheet 2 as arrows A. Therefore, the detecting head relatively traces steel tire belt 2 along a zigzag line, successively detecting steel cords (inserts) 3 in real time.

If the detecting area is partial, this combination is exchangeable with a structure in which only slit frame 5A is to run while radiant ray source 1 and detector 6 are stationary.

Slit 5 may be disposed between sheet 2 and radiant ray source 1 instead of the detector side, and may be exchanged with a collimator for forming a fine parallel beam.

Figure 3:
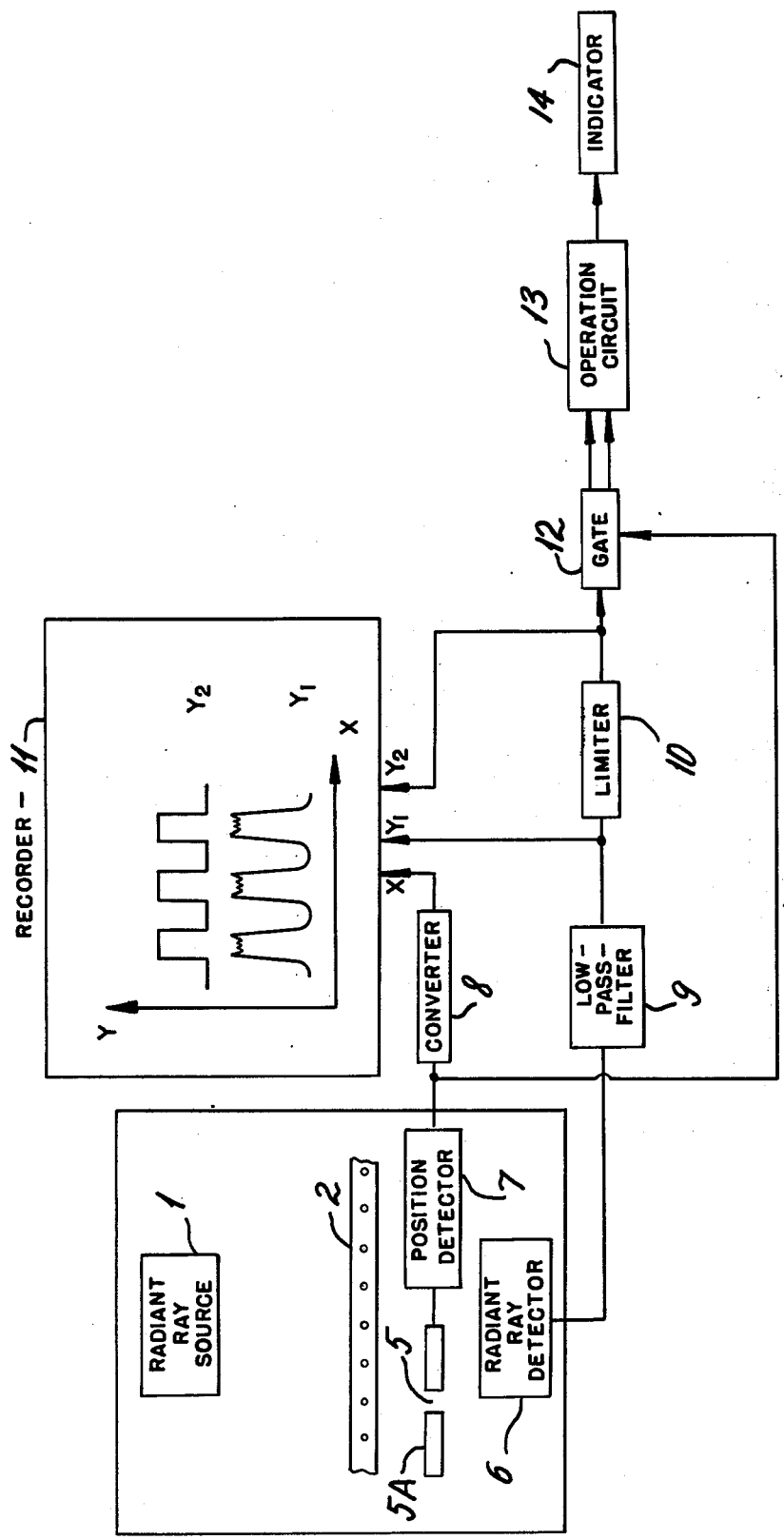
FIG. 3 is a block diagram showing the apparatus concerning with the detecting device of FIG. 2.

In any case, the relative position of slit 5 to sheet 2 is determined by a position detector 7 such as a linear encoder which is shown in FIG. 3. The position signal from position detector 7 is fed to a converter 8, for generating there the horizontal axis signal (X axis) of a display screen of a cathode ray tube or recorder 11 proportional to the slit position. The radiant ray intensity signal generated at radiant ray detector 6 is fed to a low-pass-filter 9 for smoothing the pulse-formed intensity signal into the vertical axis signal for $Y_1$ axis. Therefore, the composition of the horizontal axis signal and the vertical axis signal continuously represents the distribution of inpurities 3 (steel cords and air etc.) in matrix material 2 (calendered steel tire belt) on the display screen.

Numeral 10 designates a limiter to receive the vertical axis signal for $Y_1$ axis and to shape it into rectangular wave form signal. This rectangular wave form signal serves as a second vertical axis signal for $Y_2$, clearly indicating the steel code position. And further this signal for $Y_2$ is fed to a gate 12 as the gate signal. Gate 12 receives the position signal of position detector 7. In gate 12, each rise-up and each fall-down instant of the rectangular form signal at $Y_2$ separate off the position signal for sending the separated signals to an operation circuit 13. A linear encoder or other digital position detector is preferable for position detector 7, which generates clock pulses, but other type position detectors such as a differential transformer, potentio meter or other analogue position detector may be applicable. When a digital one is used, clock pulse trains separated by the gate signal, each of which is respectively corresponding to a steel cord width or a gap between a pair of steel cords, are successively fed to operation circuit 13 and are processed there to compute out means and-/or individual steel-cord width ratio to the matrix width, and/or the widths themselves. With additional calibration, the calender rubber thickness distributions both in the longitudinal and lateral directions can further be computed sucessively in operation circuit 13. These outputs of operation circuit 13 are displayed at an indicator 14 of either digital or graphic type, or are fed, as input data, to a computer which is not shown in the drawings.

Radiant rays (X-rays or γ-rays) irradiated from radiant ray source 1 are applied to sheet 2 and penetrate through suffering some attenuation in accordance with materials of the sheet matrix and the impurity 3, and thus penetrated radiant rays have a distribution of intensity in correspondence with the impurity disposition.

This radiant ray distribution is successively detected by scanning the assembly of radiant ray source 1, slit 5 and detector 6.

The distribution or disposition of impurity 3 such as steel cords is visually displayed on screen 11. More clear disposition of steel cords 3 without noise can be displayed in X-$Y_2$ relation.

The thickness distribution may also be displayed suitably adjusting the vertical level of the screen.

Indicator 14 indicates the outputs such as mean ratio of steel-cord width to the matrix width, thickness change, and the like.

What is claimed is:

1. Apparatus for inspecting an object to detect inserts therein comprising:
    a radiant ray source for directing a beam of radiant rays toward an object to be inspected,
    a radiant ray detector disposed at the opposite side of said object from said radiant ray source in position to receive radiant rays transmitted through said object,
    a low-pass filter for smoothing a pulse-form intensity signal from said radiant ray detector,
    means interposed between said radiant ray source and said radiant ray detector to restrict said beam of radiant rays to a fine beam of parallel rays, said beam restricting means being movable relative to said object so as to scan said object whereby rays transmitted through different parts of said object are detected successively by said radiant ray detector,
    means for detecting the position and for generating pulse signals in response to movement of said beam restricting means relative to said object, and
    two-dimensional display means receiving a positional signal from said position detecting means and the output signal of said low-pass filter and displaying a curve of which the abscissa is determined by said signal from said position indicating means to indicate the portion of the object inspected and the ordinate is determined by said signal from said radiant ray detector as modified by said low-pass filter to indicate the presence or absence of an insert in said portion.

2. Apparatus according to claim 1, in which said radiant ray beam restricting means comprises a plate of radiant ray non-transmitting material having a slit therein.

3. Apparatus according to claim 2, in which said slit is narrower than said inserts in width.

4. Apparatus according to claim 1, in which said radiant ray beam restricting means comprises a collimator.

5. Apparatus according to claim 1, in which said position detecting means comprises a linear encoder.

6. Apparatus according to claim 5, comprising a convertor receiving signals from said linear encoder and generating a horizontal axis signal which is fed to said display means.

7. Apparatus according to claim 1, in which said radiant ray source and said radiant ray detector are movable synchronously with said radiant ray beam restricting means.

8. Apparatus according to claim 7, in which said object is a running belt and in which said radiant ray source, radiant ray detector and radiant ray beam restricting means are moved back and forth transversely of the running direction of said belt so as to trace a zig-zag pattern.

9. Apparatus according to claim 1, comprising a limiter receiving the output signal of said low-pass filter and shaping it into a rectangular wave form signal indicating the existence and non-existence of said inserts in said object, a gate receiving the output of said limiter and the output of said position detector, an operational circuit connected to the output of said gate for computing out a mean valve of said inserts in said object and means for displaying said mean value.

10. Apparatus according to claim 1, comprising a limiter receiving the output signal of said low-pass filter and shaping it into a rectangular wave form signal indicating the existence and non-existence of inserts in said object, a gate receiving the output of said position detector and the output of said limiter, an operational circuit connected to the output of said gate for computing out an individual ratio of said inserts in said object, and means for displaying said ratio.

11. Apparatus according to claim 1, comprising a limiter receiving the output signal of said low-pass filter and for shaping it into a rectangular wave form signal indicating the existence and non-existence of inserts in said objects and means connecting the output of said limiter with said two-dimensional display means whereby said two-dimensional display means displays said curve of which the abscissa is determined by said signal from said position indicating means and the ordinate is determined by said signal from said low-pass filter and a second curve of rectangular wave form of which the abscissa is determined by said signal from said position indicating means and the ordinate is determined by the output of said limiter so as to display a rectangular wave curve.

12. Apparatus according to claim 1, in which the output of said low-pass filter is connected with said display means through a limiter which shapes the output of said low-pass filter into a rectangular wave form signal, whereby said curve displayed by said display means is a rectangular wave curve indicating the presence or absence of inserts in successive portions of said object as it is progressively inspected.

* * * * *